United States Patent [19]

Yanai et al.

[11] Patent Number: 4,912,090

[45] Date of Patent: Mar. 27, 1990

[54] ANTIPARASITIC MILBEMYCIN AND AVERMECTIN DERIVATIVES

[75] Inventors: Toshiaki Yanai; Kazuo Sato, both of Tokyo; Akira Nishida; Keiji Tanaka, both of Shiga, all of Japan

[73] Assignee: Sankyo Company Limited, Tokyo, Japan

[21] Appl. No.: 947,615

[22] Filed: Dec. 30, 1986

[30] Foreign Application Priority Data

Jan. 7, 1986 [JP] Japan ................................ 61-1190

[51] Int. Cl.$^4$ ...................... A61K 31/70; C07H 17/04; C07D 313/06
[52] U.S. Cl. ...................................... 514/30; 536/7.1; 549/264; 514/450; 71/88
[58] Field of Search ................... 536/7.1; 514/30, 450; 549/264, 265; 71/88

[56] References Cited

U.S. PATENT DOCUMENTS 4,530,921 7/1985 Mrozik .................... 536/7.1
4,696,922 9/1987 Sturm et al. .

FOREIGN PATENT DOCUMENTS 0136892 4/1985 European Pat. Off. .
0147852 7/1985 European Pat. Off. .
0184989 6/1986 European Pat. Off. .

*Primary Examiner*—Johnnie R. Brown
*Assistant Examiner*—Elli Peselev
*Attorney, Agent, or Firm*—Frishauf, Holtz, Goodman & Woodward

[57] ABSTRACT

8,9 and/or 14,15 epoxidized and 5-acylated milbemycins and avermectins are prepared from the parent milbemycins and avermectins by epoxidation and acylation (in either order). They have enhanced anthelmintic, acaricidal and insecticidal activities.

19 Claims, No Drawings

ANTIPARASITIC MILBEMYCIN AND AVERMECTIN DERIVATIVES

BACKGROUND TO THE INVENTION

The present invention relates to a series of new macrolide compounds which are derivatives of certain known milbemycin and avermectin derivatives. These compounds have valuable acaricidal, insecticidal and anthelmintic activities. The invention also provides methods of preparing these compounds and compositions and methods for using them.

The milbemycins are a series of macrolide compounds known to have anthelmintic, acaricidal and insecticidal activities. Milbemycin D was disclosed in U.S. Pat. No. 4,346,171, where it was referred to as "Compound B-41D", and milbemycins $A_3$ and $A_4$ were disclosed in U.S. Pat. No. 3,950,360. These compounds may be represented by the formula (A):

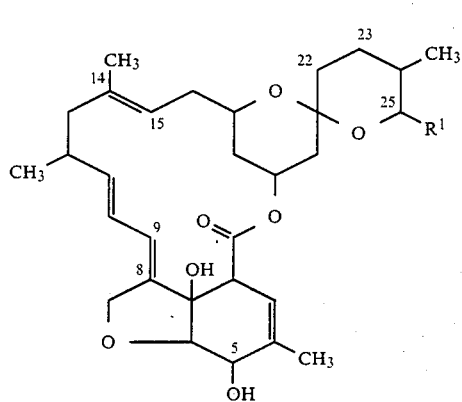

in which $R^1$ represents a methyl group, an ethyl group or an isopropyl group, these compounds being designated as milbemycin $A_3$, milbemycin $A_4$ and milbemycin D, respectively. For the avoidance of doubt, formula (A) also shows the numbering of positions of the macrolide ring system applied to those positions most relevant to the compounds of the present invention.

Subsequently, various derivatives of the original milbemycins have been prepared and their activities investigated. For example, epoxy milbemycins have been disclosed in Japanese patent applications Kokai (i.e. laid open to public inspection) No. 57-139079, 57-139080, 59-33288 and 59-36681 and in U.S. Pat. No. 4,530,921. 5-Esterified milbemycins have been disclosed in U.S. Pat. No. 4,201,861, No. 4,206,205, No. 4,173,571, No. 4,171,314, No. 4,203,976, No. 4,289,760, No. 4,457,920, No. 4,579,864 and No. 4,547,491, in European Patent Publications No. 8184, No. 102,271, No. 115,930, No. 180,539 and No. 184,989 and in Japanese patent applications Kokai No. 57-120589, 59-16894 and 61-180787.

Like the milbemycins, the avermectins are based upon the same 16-membered ring macrolide compound. The avermectins are disclosed, for example in J. Antimicrob. Agents Chemother., 15(3), 361–367 (1979). These compounds may be represented by the formula (B):

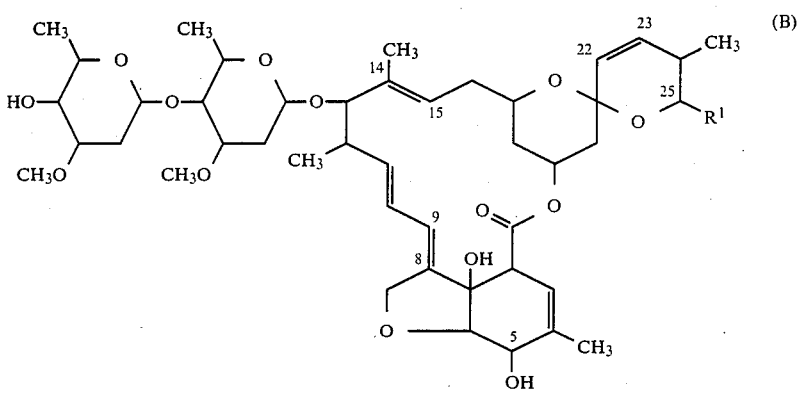

in which $R^1$ represents an isopropyl group or a sec-butyl group, these compounds being designated as avermectin $B_{1b}$ and avermectin $B_{1a}$, respectively.

22,23-Dihydroavermectins $B_{1a}$ and $B_{1b}$ may be obtained by reduction of the double bond between the 22 and 23 positions and are disclosed in U.S. Pat. No. 4,199,569.

We have now discovered that certain esterified and epoxidized derivatives of these milbemycins and avermectins have unexpectedly potent acaricidal, insecticidal and anthelmintic activities.

BRIEF SUMMARY OF INVENTION

The compounds of the invention are those compounds of formula (I):

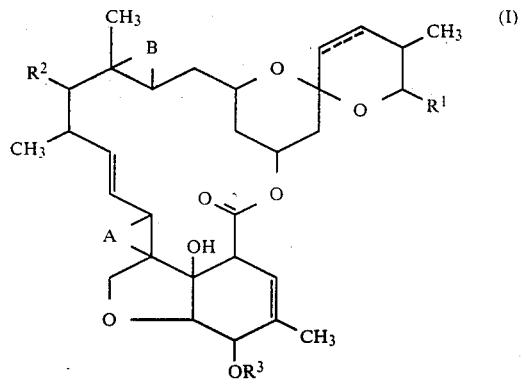

in which:

the broken line represents a single or double carbon-carbon bond between the carbon atoms at the 22 and 23 positions;

$R^1$ represents a methyl group, an ethyl group, an isopropyl group or a sec-butyl group;

R² represents a hydrogen atom or a 4'-(α-L-oleandrosyl)-α-L-oleandrosyloxy group;

R³ represents a pharmaceutically, agriculturally or veterinarily acceptable organic acid residue capable of forming an ester group;

one of A and B represents an oxygen atom; and the other of A and B represents an oxygen atom or a double bond between the two carbon atoms to which it is shown as attached.

The compounds of the invention may be prepared from a compound of formula (II):

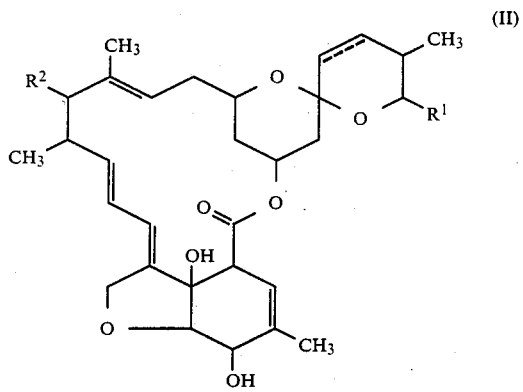

(in which the dotted line and R¹ and R² are as defined above) by subjecting said compound of formula (II) in any order to the steps:

(a) oxidation to convert at least one of the double bonds at the 8, 9 and 14, 15 positions to an epoxy group; and (b) esterification at the 5-position with an acid of formula (III):

$$R^3OH \qquad (III)$$

(in which R³ is as defined above) or with a reactive derivative thereof.

The invention still further provides an anthelmintic, acaricidal and insecticidal composition comprising an anthelmintic, acaricidal and insecticidal compound in admixture with a pharmaceutically, agriculturally, veterinarily or horticulturally acceptable carrier or diluent, wherein said compound is selected from the group consisting of compounds of formula (I).

The invention still further provides a method of treating an animal, which may be human or non-human, parasitized by a parasite selected from the group consisting of helminths, acarids and insects, which comprises applying to or administering to said animal an active compound, wherein said active compound is selected from the group consisting of compounds of formula (I).

The invention still further provides a method of protecting animals or plants from damage by parasites selected from the group consisting of acarids, helminths and insects, which comprises applying an active compound to said animals, to said plants or to seeds of said plants or to a locus including said animals, plants or seeds, wherein the active compound is selected from the group consisting of compounds of formula (I).

DETAILED DESCRIPTION OF INVENTION

Preferred classes of compounds of the present invention are as follows:

1. Where the broken line between the 22 and 23 positions represents a single bond, R¹ represents a methyl group, an ethyl group or an isopropyl group and R² represents a hydrogen atom.

2. Where the broken line between the 22 and 23 positions represents a single bond, R¹ represents an isopropyl group or a sec-butyl group and R² represents a 4'-(α-L-oleandrosyl)-α-L-oleandrosyloxy group.

3. Where the broken line between the 22 and 23 positions represents a double bond, R¹ represents an isopropyl group or a sec-butyl group and R² represents a 4'-(α-L-oleandrosyl)-α-L-oleandrosyloxy group.

R³ represents a residue of a pharmaceutically acceptable organic acid which is capable of forming an ester with the hydroxy group at the 5-position of the parent milbemycin. Examples of such organic acids include, for example, the carboxylic acids, carbonic acids, carbamic acids, sulfonic acids and phosphoric acids.

Preferred groups which may be represented by R³ include the groups having the following formulae:

$$-CO-(O)_n-R^4 \qquad 1.$$

in which:

n represents the cypher 0 or the integer 1; and

R⁴ represents a $C_1$-$C_{18}$ alkyl group, a $C_3$-$C_8$ cycloalkyl group, a $C_7$-$C_9$ aralkyl group, a $C_2$-$C_{17}$ alkenyl group, a $C_2$-$C_6$ alkynyl group, a $C_6$-$C_{10}$ aryl group or a heterocyclic group having from 5 to 10 ring atoms of which at least one is a hetero-atom selected from the group consisting of nitrogen, oxygen and sulfur atoms, said alkyl, alkenyl and alkynyl groups being unsubstituted or having at least one substituent selected from the group consisting of substituents (a):

substituents (a): alkoxy groups, halogen atoms, alkoxycarbonyl groups, carboxylic acyloxy groups, hydroxy groups, carboxy groups, amino groups, alkylamino groups, dialkylamino groups, trialkylamino groups, carboxylic acylamino groups, cyano groups, carbamoyl groups, alkylcarbamoyl groups, dialkylcarbamoyl groups, mercapto groups, alkylthio groups, alkylsulfinyl groups, alkylsulfonyl groups, nitro groups, phenoxy groups, halophenoxy groups, alkylsulfonyloxy groups, arylsulfonyloxy groups, thiocyanato groups and heterocyclic groups having 5 or 6 ring atoms of which at least one is a heteroatom selected from the group consisting of nitrogen, oxygen and sulfur atoms;

and said cycloalkyl, aralkyl and aryl groups being unsubstituted or having at least one substituent selected from the group consisting of substituents (a) and substituents (b):

substituents (b): alkyl groups, alkoxyalkyl groups and haloalkyl groups;

and said heterocyclic groups being unsubstituted or having at least one substituent selected from the group consisting of substituents (a), substituents (b) and oxygen atoms;

where groups in said substituents (a) and substituents (b) contain carbon atoms, the maximum number of carbon atoms in each such group is 9 and said groups defined in substituents (a) and substituents (b) being unsubstituted or having at least one further substituent selected from the group consisting of substituents (a) and substituents (b) provided said further substituent is not itself further substituted.

$-CO-NR^5R^6$     2.

in which $R^5$ and $R^6$ are independently selected from the group consisting of hydrogen atoms, $C_1$-$C_6$ alkyl groups, $C_2$-$C_6$ alkenyl groups, $C_7$-$C_9$ aralkyl groups and $C_6$-$C_{10}$ aryl groups, said groups being unsubstituted or having at least one substituent as defined for the corresponding group represented by $R^4$.

$-SO_2R^7$     3.

in which $R^7$ represents a $C_1$-$C_6$ alkyl group or a $C_6$-$C_{10}$ aryl group, said groups being unsubstituted or having at least one substituent as defined for the corresponding group represented by $R^4$.

$-(Y^1=)P(-Y^2-R^8)-Y^3-R^9$     4.

in which:

$Y^1$, $Y^2$ and $Y^3$ are independently selected from the group consisting of oxygen atoms and sulfur atoms; and $R^8$ and $R^9$ are independently selected from the group consisting of $C_1$-$C_6$ alkyl groups and $C_1$-$C_6$ alkyl groups having at least one substituent selected from the group consisting of substituents (a).

Where $R^4$ represents an alkyl group, this may be a straight or branched chain alkyl group having from 1 to 18 carbon atoms and examples of such groups include the methyl, ethyl, propyl, isopropyl, butyl, isobutyl, sec-butyl, t-butyl, pentyl, isopentyl, heptyl, octyl, decyl, undecyl, dodecyl, tridecyl, pentadecyl, hexadecyl, heptadecyl and octadecyl groups.

Where $R^4$ represents a cycloalkyl group, this may be a monocyclic or fused polycyclic (preferably bicyclic) ring system containing from 3 to 8 ring carbon atoms and examples include the cyclopropyl, cyclobutyl, cyclopentyl, cyclohexyl, cycloheptyl, cyclooctyl and bicyclo[2.2.1]heptyl groups.

Where $R^4$ represents an aralkyl group containing from 7 to 9 carbon atoms, examples of such groups include the benzyl, phenethyl, 3-phenylpropyl, α-methylbenzyl and α,α-dimethylbenzyl groups.

Where $R^4$ represents an alkenyl group, this may be a straight or branched chain group containing from 2 to 17, preferably from 2 to 6, carbon atoms and having at least one double bond. Examples include the vinyl, 1-propenyl, 2-propenyl, isopropenyl, 1-methyl-1-propenyl, 9-decenyl, 8-heptadecenyl, 8,11-heptadecadienyl, 8,11,14-heptadecatrienyl and 8-pentadecenyl groups.

Where $R^4$ represents an alkynyl group containing from 2 to 6 carbon atoms, this may be a straight or branched chain group and examples include the ethynyl, 1-propynyl and 2-propynyl groups.

Where $R^4$ represents an aryl group containing from 6 to 10 carbon atoms, examples of such groups include the phenyl, 1-naphthyl and 2-naphthyl groups.

Where $R^4$ represents a heterocyclic group, it contains from 5 to 10 ring atoms, of which at least one, and preferably from 1 to 3, are hetero-atoms selected from the group consisting of nitrogen, oxygen and sulfur atoms. The ring system may be a monocyclic or fused polycyclic (preferably bicyclic) ring system and examples of the heterocyclic groups which may be represented by $R^4$ include the furyl, thienyl, pyrrolyl, pyridyl, thiazolyl, isothiazolyl, oxazolyl, isooxazolyl, imidazolyl, pyrazolyl, pyranyl, triazolyl, triazinyl, quinazolyl, tetrahydrofuranyl, tetrahydrothienyl, pyrrolidinyl, thiazolidinyl, piperazinyl, morpholinyl, thiomorpholinyl, tetrahydroquinolyl, quinuclidinyl and thienofuranyl groups.

Examples of substituents which may be present on any of the above groups which may be represented by $R^4$ include: such alkyl groups as the methyl, ethyl, isopropyl and t-butyl groups; such alkoxy groups as the methoxy, ethoxy and isopropoxy groups; such alkoxyalkyl groups as the methoxymethyl group; such alkoxycarbonyl groups as the methoxycarbonyl and ethoxycarbonyl groups; such haloalkyl groups as the chloromethyl, fluoromethyl, trichloromethyl, trifluoromethyl and 2-chloroethyl groups; such halo groups as the fluoro, chloro, bromo and iodo groups; the hydroxy, carboxy and amino groups; such alkylamino and alkylammonium groups as the methylamino, dimethylamino, diethylamino, diisopropylamino and diethyl(methyl)ammonium groups; such lower aliphatic carboxylic acylamino groups as the acetamido and trifluoroacetamido groups; the cyano and carbamoyl groups; such alkylcarbamoyl groups as the methylcarbamoyl and dimethylcarbamoyl groups; such lower aliphatic carboxylic acyloxy groups as the fluoroacetoxy and trichloroacetoxy groups; such substituted lower alkoxycarbonyl groups as the $\beta,\beta,\beta$-trichloroethoxycarbonyl group; the mercapto, methylthio, thiocyanato, methanesulfinyl, methanesulfonyl, nitro, phenoxy and p-chlorophenoxy groups; such substituted alkoxy groups as the 2,2-dimethyl-1,3-dioxolanylmethoxy group; and such heterocyclic carbonyloxy groups as the 3,4-dihydro-2H-pyran-2-carbonyloxy and 3,4,5,6-diisopropylidine-D-galactouronyloxy groups; as well as the 5- and 6-membered compounds amongst the heterocyclic groups defined for $R^4$.

Where $R^5$, $R^6$, $R^7$, $R^8$ or $R^9$ represents a $C_1$-$C_6$ alkyl group, this may be a straight or branched chain group and examples include the methyl, ethyl, propyl, isopropyl, butyl, sec-butyl, isobutyl, t-butyl, pentyl, isopentyl, hexyl and isohexyl groups.

Where $R^5$, $R^6$ or $R^7$ represents an aryl group or $R^5$ or $R^6$ represents an alkenyl or aralkyl group, these may be exemplified above in relation to $R^4$.

Particularly preferred groups which may be represented by $R^3$ include the acetyl, propionyl, chloroacetyl, trichloroacetyl, trifluoroacetyl, acetoxyacetyl, chloropropionyl, chlorobenzoyl, ethoxycarbonyl, methoxycarbonyl, chloromethoxycarbonyl, dichloromethoxycarbonyl, (3,4-dihydro-2H-pyran-2-carbonyloxy) methoxycarbonyl, (3,4,5,6-diisopropylidene-D-galactouronyloxy) methoxycarbonyl, (2,2-dimethyl-1,3-dioxolanylmethoxy)methoxycarbonyl, hydroxybutyryloxymethoxycarbonyl, carboxypropionyl, (1H-1,2,4-triazol-1-yl)acetyl, diethylaminoacetyl, (iodomethyldiethylammonio)acetyl, methylcarbamoyl, ethylcarbamoyl, dimethylcarbamoyl, diethylcarbamoyl, methanesulfonyl, p-toluenesulfonyl, benzenesulfonyl, diethylthiophosphoryl, dimethylphosphoryl, diethylphosphoryl, fluorobenzoyl, butyryl, valeryl, hexanoyl, octanoyl, hexadecanoyl, isobutyryl, isovaleryl, pivaloyl, acryloyl, benzoyl, bromoacetyl, allyloxycarbonyl, iodoacetyl, propionyloxyacetyl, hydroxyacetoxyacetyl, (benzamidoacetoxy)acetyl, cinnamoyl, (trifluoromethyl)benzoyl, iodobenzoyl, toluoyl, methoxybenzoyl, dichlorobenzoyl, (chlorobenzyloxy)acetyl, (pyrrolylcarbonyloxy)acetyl, fluorobenzoyl, nicotinoyl, isonicotinoyl, picolinoyl, nitrobenzoyl and thiocyanatoacetyl groups.

Examples of various preferred compounds of the invention are given hereafter in the Examples. In addition to these, various other preferred compounds include:
8,9-Epoxy-5-O-acetylmilbemycin D
8,9-Epoxy-5-O-acetylmilbemycin A$_3$
8,9-Epoxy-5-O-acetyl-22,23-dihydroavermectin B$_{1a}$
8,9-Epoxy-5-O-acetyl-22,23-dihydroavermectin B$_{1b}$
8,9-Epoxy-5-O-acetylavermectin B$_{1a}$
8,9-Epoxy-5-O-acetylavermectin B$_{1b}$
8,9-Epoxy-5-O-propionylmilbemycin D
8,9-Epoxy-5-O-chloroacetylmilbemycin A$_3$
8,9-Epoxy-5-O-trichloroacetylmilbemycin D
8,9-Epoxy-5-O-trichloroacetyl-22,23-dihydroavermectin B$_{1a}$
8,9-Epoxy-5-O-trichloroacetylavermectin B$_{1a}$
8,9-Epoxy-5-O-trifluoroacetyl-22,23-dihydroavermectin B$_{1a}$
8,9-Epoxy-5-O-acetoxyacetylmilbemycin A$_4$
8,9-Epoxy-5-O-(α-chloropropionyl)avermectin B$_{1a}$
8,9-Epoxy-5-O-(p-chlorobenzoyl)milbemycin A$_4$
8,9-Epoxy-5-O-ethoxycarbonyl-22,23-dihydroavermectin B$_{1a}$
8,9-Epoxy-5-O-dichloromethoxycarbonylmilbemycin A$_4$
8,9-Epoxy-5-O-(3,4-dihydro-2H-pyran-2-carbonyloxy)methoxycarbonylmilbemycin D
8,9-Epoxy-5-O-(3,4,5,6-diisopropylidine-D-galactouronyloxy)methoxycarbonylmilbemycin A$_4$
8,9-Epoxy-5-O-(2,2-dimethyl-1,3-dioxolanylmethoxy)methoxycarbonylmilbemycin A$_4$
8,9-Epoxy-5-O-4'-hydroxybutyryloxymethoxycarbonylmilbemycin A$_4$
8,9-Epoxy-5-O-carboxypropionylmilbemycin A$_4$
Sodium 8,9-epoxy-5-O-carboxylatopropionylmilbemycin D
8,9-Epoxy-5-O-(1H-1,2,4-triazol-1-yl)acetylmilbemycin A$_4$
8,9-Epoxy-5-O-diethylaminoacetylmilbemycin A$_4$
8,9-Epoxy-5-O-(iodomethyldiethylammonio)acetylmilbemycin A$_4$
8,9-Epoxy-5-O-methylcarbamoylmilbemycin A$_4$
8,9-Epoxy-5-O-methanesulfonylmilbemycin A$_4$
8,9-Epoxy-5-O-p-toluenesulfonylmilbemycin D
8,9-Epoxy-5-O-diethylthiophosphorylmilbemycin D
8,9-Epoxy-5-O-dimethylphosphorylmilbemycin A$_4$
14,15-Epoxy-5-O-methoxycarbonylmilbemycin A$_4$
14,15-Epoxy-5-O-methanesulfonylmilbemycin D
8,9,14,15-Diepoxy-5-O-trichloroacetylmilbemycin A$_4$
8,9,14,15-Diepoxy-5-O-trichloroacetyl-22,23-dihydroavermectin B$_{1a}$
8,9,14,15-Diepoxy-5-O-p-fluorobenzoylavermectin B$_{1a}$
8,9,14,15-Diepoxy-5-O-methanesulfonylmilbemycin A$_4$ The most preferred compounds of the invention are:
8,9-epoxy-5-O-propionylmilbemycin A$_{4+3}$
8,9-epoxy-5-O-α-chloropropionylmilbemycin A$_{4+3}$ and
8,9-epoxy-5-O-trifluoroacetylmilbemycin A$_4$.

Preparation of the compounds of the invention may be carried out as indicated in the following reaction scheme:

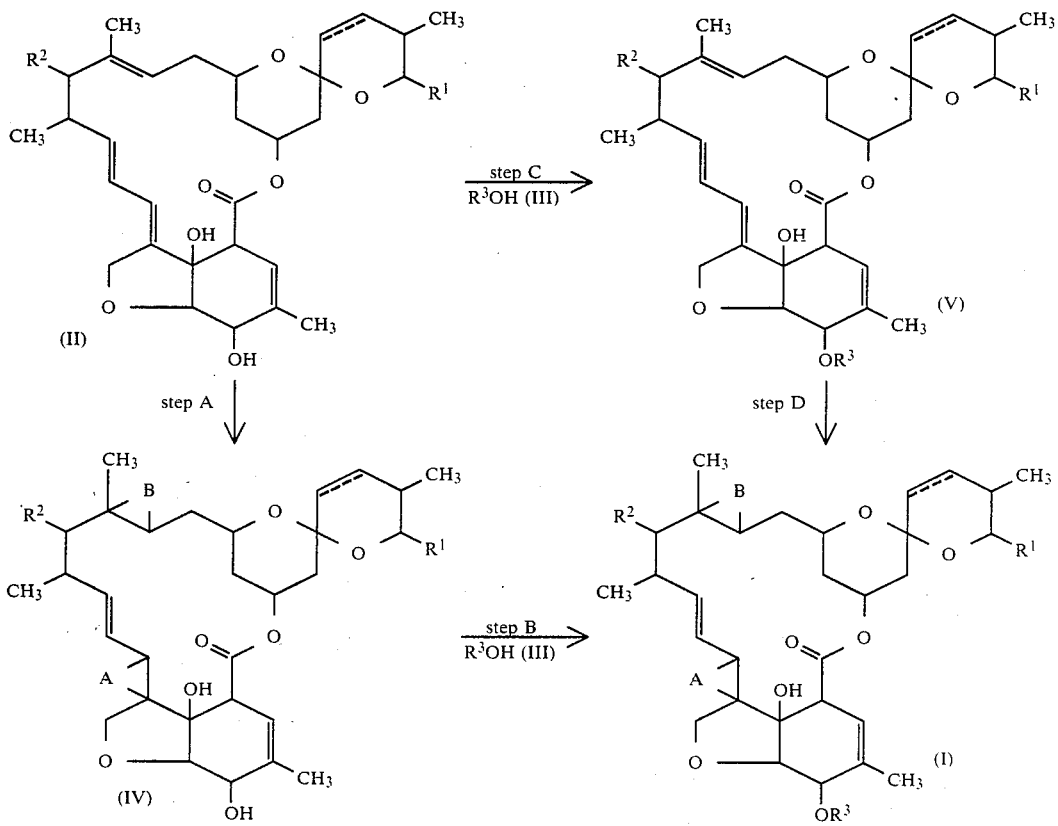

In the above formulae, R$^1$, R$^2$, R$^3$, A, B and the broken line are as defined above.

STEPS A AND D

In these steps, the compounds of formulae (II) and (V), respectively, are epoxidized with a mild oxidizing agent to convert one or both of the double bonds at the 8,9 and 14,15 positions to an epoxy group. Certain of the compounds of formula (IV), their use and the preparative method involved in Step A are disclosed in Japanese Patent Applications Kokai No. 57-139079, 57-139080 and 59-36681 and in U.S. Pat. No. 4,530,921, the disclosures of which are incorporated herein by reference.

In these steps, the mild oxidizing agent is preferably either: a peracid, such as m-chloroperbenzoic acid; or an alkyl hydroperoxide, such as t-butyl hydroperoxide, in association with a metal acetylacetonate, such as vanadium oxyacetylacetonate, as catalyst. Such epoxidation reactions are well known for this type of compound and there is no particular limitation on the nature of the oxidizing agent employed. However, where it is desired to epoxidize only the 8,9 double bond, we prefer to carry this out using from 1 to 2 equivalents of the alkyl hydroperoxide catalyzed by a metal acetylacetonate. Where it is desired to epoxidize only the 14,15 double bond, it is desirable to use from 1 to 2 equivalents of a peracid. Where it is desired to epoxidize both the 8,9 and 14,15 double bonds to produce a diepoxy derivative, there is no particular limitation on the nature of the oxidizing agent, although we prefer to use from 2 to 3 equivalents of such an oxidizing agent. If a much greater excess of oxidizing agent is used, the oxidation reaction can give rise to the 3,4,8,9,14,15-triepoxy derivative as a by-product.

The reaction is preferably carried out in the presence of a solvent, the nature of which is not critical, provided that it does not interfere with the reaction and is not readily oxidized under conditions of the reaction. Suitable solvents include, for example: hydrocarbons, particularly aliphatic and aromatic hydrocarbons, such as hexane, benzene or toluene; and halogenated hydrocarbons, particularly halogenated aliphatic hydrocarbons, such as methylene chloride or chloroform. The reaction will take place over a wide range of temperatures and the precise temperature chosen is not critical to the invention; however, we generally find it convenient to carry out the reaction at a temperature of from 0° to 40° C. and preferably at about room temperature. The time required for the reaction may vary widely, but a period of from 1 to 6 hours will normally suffice.

STEPS B AND C

In these steps, the compound of formula (IV) or (II), respectively, is acylated at its 5-position with a carboxylic acid of formula (III) or with a reactive derivative thereof, to give a compound of formula (I) of (V) respectively.

Some of the compounds of formula (V), their use and their preparation as in Step C are known from Japanese Patent Application Kokai No. 57-139081 and 59-36681 and from U.S. Pat. No. 4,173,571 and 4,171,314, the disclosures of which are incorporated herein by reference.

The acylation reaction may be carried out by methods well known for this type of reaction using either the free acid of formula (III) or a reactive derivative thereof. Examples of reactive derivatives include: acid halides, such as the acid chloride, acid bromide or acid iodide; acid anhydrides; mixed acid anhydrides; active esters, such as the p-nitrobenzyl ester; and active amides.

The reaction is preferably carried out in the presence of a solvent, the nature of which is not critical, provided that it has no adverse effect upon the reaction. Examples of suitable solvents include: hydrocarbons, which may be aliphatic or aromatic, such as hexane, benzene or toluene; halogenated hydrocarbons, particularly halogenated aliphatic hydrocarbons, such as methylene chloride or chloroform; ethers, such as diethyl ether, tetrahydrofuran or dioxane; ketones, such as acetone or methyl ethyl ketone; nitriles, such as acetonitrile; and esters, such as ethyl acetate. The reaction will take place over a wide range of temperatures and the precise temperature chosen is not critical to the invention. However, we generally find it convenient to carry out the reaction at a temperature of from 0° to 80° C. and more preferably at a temperature of from 10° to 30° C. The time required for the reaction may vary widely, depending upon many factors; however, at a temperature within the suggested ranges, a period of from 1 to 6 hours will normally suffice.

We generally prefer to employ from 1 to 10 equivalents, more preferably from 1.5 to 4 equivalents, of the acid (III) or its reactive derivative, per mole of the compound of formula (II) or (IV).

Where the acid (III) itself is employed, the reaction is preferably effected in the presence of a dehydrating agent, such as dicyclohexylcarbodiimide, p-toluenesulfonic acid or sulfuric acid. Where a reactive derivative of the acid (III) is employed, we prefer to carry out the reaction in the presence of a base, which serves to accelerate the reaction. Examples of suitable bases include: such organic bases as pyridine, triethylamine and 4-dimethylaminopyridine; and such inorganic bases as potassium carbonate or sodium carbonate.

After completion of each or both of the steps of the reaction sequence, the resulting product can be recovered from the reaction mixture by conventional means and, if necessary, may be further purified by such conventional means as the various chromatography techniques, particularly column chromatography.

Surprisingly, we have found that the yield in epoxidation Step D is very much better than that in the known epoxidation Step A. Accordingly, the preferred reaction sequence comprises Step C followed by Step D.

The starting material of formula (II) may be a single isolated compound or it may be a mixture of two or more such compounds, which may be used without separation. For example, mixtures of milbemycins $A_3$ and $A_4$ are readily available and may easily be used.

The compounds of the invention have a strong acaricidal activity against, for example, adults, imagos and eggs of Tetranychus, Panonychus (e.g. Panonychus ulmi and *Panonychus citri*), *Aculopa pelekassi* and rust mites, which are parasitic to fruit trees, vegetables and flowers. They are also active against Ixodidae, Dermanyssidae and Sarcoptidae, which are parasitic to animals. Further, they are active against: exoparasites, such as Oestrus, Lucilia, Hypoderma, Gautrophilus, lice and fleas, which are parasitic to animals and birds, particularly livestock and poultry; domestic insects, such as cockroaches and houseflies; and various harmful insects in agricultural and horticultural areas, such as aphids and larval Lepidoptera. They are also effective against Meloidogyne in the soil, Bursaphelenchus and Phizoglyphus. They are also effective against insects of the orders Coleoptera, Homoptera, Heteroptera, Diptera, Thysanoptera, Orthoptera, Anoplura, Siphonaptera, Mallophage, Thysanura, Isoptera, Psocoptera, and Hymenoptera.

The compounds of the invention equally can be used to control other plant-damaging insects, particularly insects that damage plants by eating them. The compounds can be used to protect both ornamental plants and productive plants, particularly cotton (e.g. against Spodoptera littoralis and Heliothis virescens), as well as vegetable crops (e.g. against Leptinotarsa decemlineata and Myzus persicae) and rice crops (e.g. against Chilo suppressalis and Laodelphax).

The activity of the compounds of the invention is pronounced, both systemically and by contact. Accordingly, the compounds are very effective against sucking insects, especially sucking insects of the order Homoptera and most particularly the family Aphididae (such as Aphis fabae, Aphis craccivora and Myzus persicae), which are difficult to control with known compositions.

Accordingly, the compounds of the invention can be used to treat all manner of plants (as well as the seeds from which such plants are grown and the environment, whether for growth or storage, containing such plants) to protect them from insects such as those exemplified above. Such plants include cereals (e.g. maize or rice), vegetables (e.g. potatoes or soybeans), fruits and other plants (e.g. cotton).

The compounds of the invention can similarly be used to protect animals from a variety of ectoparasites, by applying the compounds to the animals or to the animals' environment, e.g. livestock housing, animal boxes, abattoirs, pasture land and other grasslands, as well as to any other places liable to be infested. The compounds may also be applied to external parts of the animals, preferably before they are infested.

Moreover, the compounds of the invention are effective against various parasitical helminths. These parasites can attack livestock, poultry and pet animals (such as pigs, sheep, goats, cows, horses, dogs, cats and fowl) and can cause grave economic damage. Among the helminths, the nematodes in particular often cause serious infection. Typical genera of nematodes which are parasitic on these animals and against which the compounds of the invention are effective include:

Haemonchus,
Trichostrongylus,
Ostertagia,
Nematodirus,
Cooperia,
Ascaris,
Bunostomum,
Oesophagostomum,
Chabertia,
Trichuris,
Strongylus,
Trichonema,
Dictyocaulus,
Capillaria,
Heterakis,
Toxocara,
Ascaridia,
Oxyuris,
Ancylostoma,
Uncinaria,
Toxascaris and
Parascaris.

Certain parasitical species of the genera Nematodirus, Cooperia and Oesophagostomum attack the intestines, while certain species of the genera Haemonchus and Ostertagia parasitize the stomach, and parasites belonging to the genus Dictyocaulus are found in the lungs. Parasites belonging to the families Filariidae and Setariidae are found in internal tissues and organs, for example, the heart, the blood vessels, the subcutaneous tissues and the lymphatic vessels. The compounds of the invention are active against all these parasites.

The compounds of the invention are also effective against parasites which infect humans. Typical of the parasites which may most commonly be found in the digestive tracts of human beings are parasites of the genera Ancylostoma, Necator, Ascaris, Strongyloides, Trichinella, Capillaria, Trichuris and Enterobius. The compounds are also active against parasites of the genera Wuchereria, Brugia, Onchocerca and Loa of the family Filariidae (which are found in blood, tissues and organs other than the digestive tract and are medically important), parasites of the genus Dracunculus of the family Dracunculidae and parasites of the genera Strongyloides and Trichinella, which in a particular state may parasitize outside the intestinal tract, although they are essentially intestinal parasites.

The form of the compositions of the invention and the nature of the carriers or diluents employed in them will vary depending upon the intended use of the composition. For example, where the compounds of the invention are to be employed as anthelmintics, they are preferably administered orally, parenterally or topically and the form of compositions chosen will be appropriate to the intended route of administration.

For oral administration, the composition of the invention is preferably in the form of a liquid drink comprising a non-toxic solution, suspension or dispersion of the active compound in admixture with a suspending agent (such as bentonite), a wetting agent or other diluents, preferably in water or another non-toxic solvent. The drink, in general, also contains an anti-foaming agent. The active compound would normally be present in the drink in an amount of from 0.01 to 0.5% by weight, more preferably from 0.01 to 0.1% by weight.

Compositions for oral administration may also be in the form of dry solids, preferably in unit dosage form, such as capsules, pills or tablets containing the desired amount of the active compound. These compositions may be prepared by mixing the active compound uniformly with suitable diluents, fillers, disintegrators and/or binding agents, for example starch, lactose, talc, magnesium stearate and vegetable gum. The weight and contents of the preparation will vary widely, depending upon the nature of the animal to be treated, the degree of infection, the nature of the parasite and the body weight of the animal to be treated.

The compounds may also be administered as an additive to animal feedstuffs, in which case they may be dispersed uniformly in the feedstuffs, used as a top dressing or used in the form of pellets. The content of active compound in the feedstuff is preferably from 0.0001 to 0.02%, in order to achieve the desired anthelmintic activity.

For parenteral administration, the compound of the invention is preferably dissolved or suspended in a liquid vehicle, preferably a vegetable oil, such as peanut oil or cottonseed oil. Where the compound is a salt of a compound of formula (II), the liquid vehicle may be water or another aqueous medium. Depending upon the animal to be treated, the injection may be subcutaneous or into the proventriculus, a muscle or the trachea. Such preparations would normally contain the active compound at a concentration of from 0.05 to 50% by weight.

The compounds of the invention may also be administered topically in admixture with a suitable carrier, such as dimethyl sulphoxide or a hydrocarbon solvent. Such preparations would be applied directly to the outside of the animal by spraying (e.g. by a hand spray or in spray races), by dipping (e.g. in a plunge dip), by a pour-on solution or by manual methods (e.g. hand-dressing).

The dose of active compound may be varied, depending upon the nature of the animal to be treated, and the nature and degree of parasitic infection. However, best results for oral administration are achieved when the dose is from 0.01 to 100 mg, more preferably from 0.5 to 50 mg. per 1 kg body weight. The compound may be administered in a single dose or in divided doses for a relatively short period, such as from 1 to 5 days.

Where the composition of the invention is intended for agricultural or horticultural use, a variety of forms and formulations is possible. For example, the composition may be formulated as dusts, coarse dusts, soluble powders, microgranules, fine microgranules, wettable powders, dilute emulsions, emulsifiable concentrates, aqueous or oily suspensions, dispersions or solutions (which may be directly sprayable or for dilution), aerosols or capsules in, for example, polymeric substances. The carrier employed may be natural or synthetic and organic or inorganic; it is generally employed to assist the active compound to reach the substrate to be treated, and to make it easier to store, transport or handle the active compound. Solid, liquid and gaseous carriers may be employed, chosen from carriers well known in the art for use with compositions of this type.

Such formulations may be prepared by conventional means, e.g. by intimate mixing and/or grinding of the active ingredient(s) with the carrier or diluent, e.g. solvent, solid carrier or, optionally, surface-active agent.

Suitable solvents include: aromatic hydrocarbons, preferably the $C_8$ to $C_{12}$ fractions from petroleum distillation, such as xylene mixtures or substituted naphthalenes; esters of phthalic acid, such as dibutyl or dioctyl phthalate; aliphatic hydrocarbons, such as cyclohexane or the paraffins; alcohols and glycols or esters thereof, such as ethanol, ethylene glycol, ethylene glycol monomethyl ether or ethylene glycol monoethyl ether; ketones, such as cyclohexanone; strongly polar solvents, such as N-methyl-2-pyrrolidone, dimethyl sulfoxide or N,N-dimethylformamide; optionally epoxidized vegetable oils, such as epoxidized coconut oil or soybean oil; and water.

Solid carriers, which may be used, for example, in dusts and dispersible powders, include natural mineral fillers, such as calcite, talc, kaolin, montmorillonite or attapulgite. In order to improve the physical properties of the composition, it is also possible to add highly dispersed silicic acid or highly dispersed absorbent polymers. Suitable granulated adsorptive carriers may be porous (such as pumice, ground brick, sepiolite or bentonite) or non-porous (such as calcite or sand). A wide variety of pregranulated materials, organic or inorganic, may also be used; examples include dolomite and ground plant residues.

Surface-active agents which may be used are well known in the art and may be non-ionic, cationic or anionic agents having good emulsifying, dispersing and wetting properties. Mixtures of such agents may also be used.

Compositions may also contain stabilizers, anti-foaming agents, viscosity regulators, binders or adhesives or any combination thereof, as well as fertilizers or other active substances to achieve special effects.

Pesticidal compositions will generally contain: from 0.01 to 99%, more preferably from 0.1 to 95%, by weight of the active compound; from 1 to 99.99% of a solid or liquid additive; and from 0 to 25%, more preferably from 0.1 to 25%, of a surface-active agent. Whereas commercial products are generally sold as concentrated compositions, they are generally diluted by the end-user to a concentration of from 0.001 to 0.0001% by weight (from 10 to 1 ppm).

The compounds of the invention have, surprisingly, been found to be most especially effective against mites on plants.

The invention is further illustrated by the following Examples, of which Examples 1-55 illustrate the preparation of various compounds of the invention and Examples 56 and 57 illustrate their biological activity. Where mixtures of compounds, e.g. milbemycins $A_4 + A_3$, are used, the ratios indicated in association with them are molar ratios. In all column chromatography reported hereafter, the eluent used was a 3:1 by volume mixture of hexane and ethyl acetate.

EXAMPLE 1

8,9-Epoxy-5-O-acetylmilbemycin $A_4$ ($R^1 = C_2H_5$, $R^2 = H$, $R^3 = $ acetyl)

0.55 ml of a 3 molar toluene solution of t-butyl hydroperoxide was added dropwise to a solution of 638 mg of 5-O-acetylmilbemycin $A_4$ and 30 mg of vanadium oxyacetylacetonate in 22 ml of dry benzene, whilst ice-cooling, and then the mixture was allowed to stand at room temperature for 2 hours. The reaction mixture was then cooled with ice, poured into an aqueous solution of sodium sulfite and extracted with ethyl acetate. The extracts were washed with water and then with a saturated aqueous solution of sodium chloride, after which they were dried over anhydrous magnesium sulfate, and the solvent was distilled off under reduced pressure. The residue was subjected to column chromatography through silica gel, to give 353 mg of the title compound.

Mass spectrum (m/z): 600 ($M^+$), 584 ($M^+ - H_2O$), 540 ($M^+ + 1 - H_2O - COCH_3$).

Nuclear Magnetic Resonance Spectrum (270 MHz, $CDCl_3$) δ ppm:

3.08 (1H, doublet of triplets, J=2.9 & 8.7 Hz, $C_{25}H$);
3.37 (1H, quartet, J=2.6 Hz, $C_2H$);
3.57 (1H, doublet, J=9.6 Hz, $C_9H$);
3.64 (1H, multiplet, $C_{17}H$);
3.83 (1H, singlet, $C_7OH$);
3.90 (1H, doublet, J=11.2 Hz, $C_{27}H$);
4.23 (1H, doublet, J=4.8 Hz, $C_6H$);
4.39 (1H, doublet, J=11.2 Hz, $C_{26}H$);
4.98 (1H, doublet of doublets, J=9.3 & 9.6 Hz, $C_{10}H$);
5.08 (1H, multiplet, $C_{15}H$);
5.28 (1H, multiplet, $C_{19}H$);
5.48 (1H, multiplet, $C_3H$);
5.64 (1H, multiplet, $C_5H$);
5.85 (1H, doublet of doublets, J=9.3 & 14 Hz, $C_{11}H$).

Following the procedure described in Example 1, the compounds of Examples 2 to 43 were prepared. These compounds may be represented by the following formula (Ia):

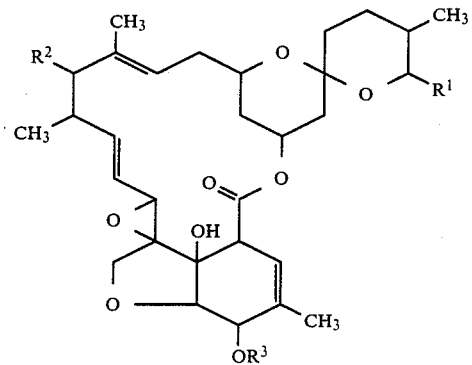

(Ia)

in which $R^1$, $R^2$ and $R^3$ are as defined in the following Table. In this Table and hereafter, the nuclear magnetic resonance (NMR) results are given only for the $C_9$ hydrogen atom and the abbreviations used are as follows:

d = doublet
dd = doublet of doublets
m = multiplet.

| Examples | $R^1$ $R^2$ $R^3$ | m/z NMR ($C_9H$) |
|---|---|---|
| 2 | $R^1 = C_2H_5 + CH_3(2.6:1)$<br>$R^2 = H$<br>$R^3 = COC_2H_5$ | m/z: 614 (M$^+$, assigned to $R^1 = C_2H_5$)<br>NMR: 3.56 (1 H, d, J = 9.5 Hz, assigned to $R^1 = CH_3$), 3.57 (1 H, d, J = 9.5 Hz, assigned to $R^1 = C_2H_5$) |
| 3 | $R^1 = C_2H_5 + CH_3(2.6:1)$<br>$R^2 = H$<br>$R^3 = COC_3H_7$ | m/z: 628 (M$^+$, assigned to $R^1 = C_2H_5$)<br>NMR: 3.56 (1 H, d, J = 9.5 Hz, assigned to $R^1 = CH_3$), 3.57 (1 H, d, J = 9.5 Hz, assigned to $R^1 = C_2H_5$) |
| 4 | $R^1 = C_2H_5 + CH_3(1.1:1)$<br>$R^2 = H$<br>$R^3 = COC_4H_9$ | m/z: 642 (M$^+$, assigned to $R^1 = C_2H_5$)<br>NMR: 3.56 (1 H, d, J = 9.5 Hz, assigned to $R^1 = CH_3$), 3.57 (1 H, d, J = 9.5 Hz, assigned to $R^1 = C_2H_5$) |
| 5 | $R^1 = C_2H_5 + CH_3(1.8:1)$<br>$R^2 = H$<br>$R^3 = COC_5H_{11}$ | m/z: 656 (M$^+$, assigned to $R^1 = C_2H_5$)<br>NMR: 3.56 (1 H, d, J = 9.5 Hz, assigned to $R^1 = CH_3$), 3.57 (1 H, d, J = 9.5 Hz, assigned to $R^1 = C_2H_5$) |
| 6 | $R^1 = C_2H_5 + CH_3(1.5:1)$<br>$R^2 = H$<br>$R^3 = COC_7H_{15}$ | m/z: 640 (M$^+$, assigned to $R^1 = C_2H_5$)<br>NMR: 3.56 (1 H, d, J = 9.5 Hz, assigned to $R^1 = CH_3$, 3.57 (1 H, d, J = 9.5 Hz, assigned to $R^1 = C_2H_5$) |
| 7 | $R^1 = C_2H_5 + CH_3(2.2:1)$<br>$R^2 = H$<br>$R^3 = COC_{15}H_{31}$ | m/z: 796 (M$^+$, assigned to $R^1 = C_2H_5$)<br>NMR: 3.56 (1 H, d, J = 9.5 Hz, assigned to $R^1 = CH_3$, 3.57 (1 H, d, J = 9.5 Hz, assigned to $R^1 = C_2H_5$) |
| 8 | $R^1 = C_2H_5 + CH_3(1.6:1)$<br>$R^2 = H$<br>$R^3 = COCH(CH_3)_2$ | m/z: 628 (M$^+$, assigned to $R^1 = C_2H_5$)<br>NMR: 3.59 (1 H, d, J = 9.5 Hz, assigned to $R^1 = CH_3$), 3.60 (1 H, d, J = 9.5 Hz, assigned to $R^1 = C_2H_5$) |
| 9 | $R^1 = C_2H_5 + CH_3(3.4:1)$<br>$R^2 = H$<br>$R^3 = COC(CH_3)_3$ | m/z: 642 (M$^+$, assigned to $R^1 = C_2H_5$)<br>NMR: 3.56 (1 H, d, J = 9.35 Hz, assigned to $R^1 = CH_3$), 3.57 (1 H, d, J = 9.35 Hz, assigned to $R^1 = C_2H_5$) |
| 10 | $R^1 = C_2H_5 + CH_3(1.8:1)$<br>$R^2 = H$<br>$R^3 = COCH=CH_2$ | m/z: 612 (M$^+$, assigned to $R^1 = C_2H_5$)<br>NMR: 3.56 (1 H, d, J = 9.5 Hz, assigned to $R^1 = CH_3$), 3.57 (1 H, d, J = 9.5 Hz, assigned to $R^1 = C_2H_5$) |
| 11 | $R^1 = C_2H_5 + CH_3(1.1:1)$<br>$R^2 = H$<br>$R^3 = COC_6H_5$ | m/z: 540 (M$^+$ +1-COC$_6$H$_5$—H$_2$O, assigned to $R^1 = C_2H_5$)<br>NMR: 3.57 (1 H, d, J = 9.5 Hz, assigned to $R^1 = CH_3$), 3.58 (1 H, d, J = 9.5 Hz, assigned to $R^1 = C_2H_5$) |
| 12 | $R^1 = C_2H_5$<br>$R^2 = H$<br>$R^3 = COCH_2Cl$ | m/z: 634 (M$^+$)<br>NMR: 3.57 (1 H, d, J = 9.35 Hz) |
| 13 | $R^1 = C_2H_5 + CH_3(2.6:1)$<br>$R^2 = H$<br>$R^3 = COCH_2Br$ | m/z: 678 (M$^+$, assigned to $R^1 = C_2H_5$ & Br = 79)<br>NMR: 3.56 (1 H, d, J = 9.5 Hz, assigned to $R^1 = CH_3$), 3.57 (1 H, d, J = 9.5 Hz, assigned to $R^1 = C_2H_5$) |
| 14 | $R^1 = C_2H_5 + CH_3(2:1)$<br>$R^2 = H$<br>$R^3 = COCCl_3$ | m/z: 702 (M$^+$, assigned to $R^1 = C_2H_5$ & Cl = 35)<br>NMR: 3.57 (1 H, d, J = 9.5 Hz, assigned to $R^1 = CH_3$), 3.59 (1 H, d, J = 9.5 Hz, assigned to $R^1 = C_2H_5$) |
| 15 | $R^1 = C_2H_5 + CH_3(4:1)$<br>$R^2 = H$<br>$R^3 = COCHClCH_3$ | m/z: 648 (M$^+$, assigned to $R^1 = C_2H_5$ & Cl = 35)<br>NMR: 3.56 (1 H, d, J = 9.3 Hz, assigned to $R^1 = CH_3$), 3.57 (1 H, d, J = 9.3 Hz, assigned to $R^1 = C_2H_5$) |
| 16 | $R^1 = C_2H_5 + CH_3(1.8:1)$<br>$R^2 = H$<br>$R^3 = COOC_2H_5$ | m/z: 648 (M$^+$, assigned to $R^1 = C_2H_5$)<br>NMR: 3.56 (1 H, d, J = 9.35 Hz, assigned to $R^1 = CH_3$), 3.57 (1 H, d, J = 9.35 Hz, assigned to $R^1 = C_2H_5$) |
| 17 | $R^1 = C_2H_5 + CH_3(2:1)$<br>$R^2 = H$<br>$R^3 = COOCH_2CH=CH_2$ | m/z: 642 (M$^+$, assigned to $R^1 = C_2H_5$)<br>NMR: 3.56 (1 H, d, J = 9.5 Hz, assigned to $R^1 = CH_3$) 3.57 (1 H, d, J = 9.5 Hz, assigned to $R^1 = C_2H_5$) |
| 18 | $R^1 = C_2H_5$<br>$R^2 = H$<br>$R^3 = COOCH_2Cl$ | m/z: 650 (M$^+$, assigned to Cl = 35)<br>NMR: 3.58 (1 H, d, J = 9.5 Hz) |
| 19 | $R^1 = C_2H_5 + CH_3(1.7:1)$<br>$R^2 = H$<br>$R^3$ = 3,4-dihydro-2H-pyran-2-carbonloxy-methoxycarbonyl | m/z: 742 (M$^+$, assigned to $R^1 = C_2H_5$)<br>NMR: 3.57 (1 H, d, J = 9.7 Hz) |
| 20 | $R^1$ = sec-C$_4$H$_9$ + i-C$_3$H$_7$(8:1)<br>$R^2$ = 4'-(α-L-oleandrosyl)-α-L-oleandrosyloxy<br>$R^3 = COC_2H_5$ | NMR: 3.61 (1 H, d, J = 9.5 Hz) C$_3$H: 5.39 (1 H, m)<br>C$_{10}$H: 4.90 (1 H, dd, J = 5.9 & 9.5 Hz)<br>C$_{15}$H: 5.11 (1 H, d, J = 9.4 Hz) |
| 21 | $R^1 = C_2H_5 + CH_3(2.6:1)$ | m/z: 726 (M$^+$, assigned to |

-continued

| Examples | $R^1$ $R^2$ $R^3$ | m/z NMR (C9H) |
|---|---|---|
| | $R^2 = H$ $R^3 = COCH_2I$ | $R^1 = C_2H_5$ NMR: 3.56 (1 H, d, J = 9.8 Hz, assigned to $R^1 = CH_3$), 3.57 (1 H, d, J = 9.8 Hz, assigned to $R^1 = C_2H_5$) |
| 22 | $R^1 = C_2H_5 + CH_3(2.2:1)$ $R^2 = H$ $R^3 = COCH_2OCOCH_3$ | m/z: 658 (M$^+$, assigned to $R^1 = C_2H_5$) NMR: 3.56 (1 H, d, J = 9.8 Hz, assigned to $R^1 = CH_3$), 3.57 (1 H, d, J = 9.5 Hz, assigned to $R^1 = C_2H_5$) |
| 23 | $R^1 = C_2H_5 + CH_3(2.2:1)$ $R^2 = H$ $R^3 = COCH_2OCOC_2H_5$ | m/z: 672 (M$^+$, assigned to $R^1 = C_2H_5$) NMR: 3.56 (1 H, d, J = 9.5 Hz, assigned to $R^1 = CH_3$), 3.57 (1 H, d, J = 9.5 Hz, assigned to $R^1 = C_2H_5$) |
| 24 | $R^1 = C_2H_5 + CH_3(2.2:1)$ $R^2 = H$ $R^3 = COCH_2OCOCH_2OH$ | m/z: 674 (M$^+$, assigned to $R^1 = C_2H_5$) NMR: 3.56 (1 H, d, J = 9.5 Hz, assigned to $R^1 = CH_3$), 3.57 (1 H, d, J = 9.5 Hz, assigned to $R^1 = C_2H_5$) |
| 25 | $R^1 = C_2H_5 + CH_3(2.2:1)$ $R^2 = H$ $R^3 = COCH_2OCOCH_2NHCOC_6H_5$ | m/z: 541 (M$^+$ $-236$, assigned to $R^1 = C_2H_5$) NMR: 3.56 (1 H, d, J = 9.5 Hz, assigned to $R^1 = CH_3$), 3.57 (1 H, d, J = 9.5 Hz, assigned to $R^1 = C_2H_5$) |
| 26 | $R^1 = C_2H_5 + CH_3(2.2:1)$ $R^2 = H$ $R^3 = CONHCH_3$ | m/z: 615 (M$^+$, assigned to $R^1 = C_2H_5$) NMR: 3.57 (1H, d, J = 9.5 Hz, assigned to $R^1 = CH_3$), 3.59 (1 H, d, J = 9.5 Hz, assigned to $R^1 = C_2H_5$) |
| 27 | $R^1 = C_2H_5 + CH_3(3:1)$ $R^2 = H$ $R^3 = COCH=CH-C_6H_5$ | m/z: 688 (M$^+$, assigned to $R^1 = C_2H_5$) NMR: 3.57 (1 H, d, J = 9.5 Hz, assigned to $R^1 = CH_3$), 3.59 (1 H, d, J = 9.5 Hz, assigned to $R^1 = C_2H_5$) |
| 28 | $R^1 = C_2H_5$) $R^2 = H$ $R^3 = CO-(p-CF_3-C_6H_4)$ | m/z: 730 (M$^+$) NMR: 3.60 (1 H, d, J = 9.5 Hz) |
| 29 | $R^1 = C_2H_5$ $R^2 = H$ $R^3 = CO-(p-Cl-C_6H_4)$ | m/z: 696 (M$^+$) NMR: 3.59 (1 H, d, J = 9.5 Hz) |
| 30 | $R^1 = C_2H_5$ $R^2 = H$ $R^3 = CO-(m-Cl-C_6H_4)$ | m/z: 696 (M$^+$) NMR: 3.59 (1 H, d, J = 9.5 Hz) |
| 31 | $R^1 = C_2H_5 + CH_3(2.2:1)$ $R^2 = H$ $R^3 = CO-(p-I-C_6H_4)$ | m/z: 788 (M$^+$, assigned to $R^1 = C_2H_5$) NMR: 3.57 (1 H, d, J = 9.2 Hz, assigned to $R^1 = CH_3$), 3.59 (1 H, d, J = 9.2 Hz, assigned to $R^1 = C_2H_5$) |
| 32 | $R^1 = C_2H_5$ $R^2 = H$ $R^3 = CO-(p-CH_3-C_6H_4)$ | m/z: 676 (M$^+$) NMR: 3.58 (1 H, d, J = 9.5 Hz) |
| 33 | $R^1 = C_2H_5 + CH_3(2.3:1)$ $R^2 = H$ $R^3 = CO-(p-OCH_3-C_6H_4)$ | m/z: 629 (M$^+$, assigned to $R^1 = C_2H_5$) NMR: 3.57 (1 H, d, J = 9.5 Hz, assigned to $R^1 = CH_3$), 3.58 (1 H, d, J = 9.5 Hz, assigned to $R^1 = C_2H_5$) |
| 34 | $R^1 = C_2H_5$ $R^2 = H$ $R^3 = CO-(2,4-diCl-C_6H_3)$ | m/z: 730 (M$^+$, assigned to Cl = 35) NMR: 3.59 (1 H, d, J = 9.5 Hz) |
| 35 | $R^1 = C_2H_5 + CH_3(2.3:1)$ $R^2 = H$ $R^3 = COCH_2O-(p-Cl-C_6H_4)$ | m/z: 726 (M$^+$, assigned to $R^1 = C_2H_5$) NMR: 3.56 (1 H, d, J = 9.5 Hz, assigned to $R^1 = CH_3$), 3.57 (1 H, d, J = 9.5 Hz, assigned to $R^1 = C_2H_5$) |
| 36 | $R^1 = C_2H_5 + CH_3(2.3:1)$ $R^2 = H$ $R^3 = COCH_2OCO-(2-pyrrolyl)$ | m/z: 709 (M$^+$, assigned to $R^1 = C_2H_5$) NMR: 3.55 (1 H, d, J = 9.5 Hz, assigned to $R^1 = CH_3$), 3.56 (1 H, d, J = 9.5 Hz, assigned to $R^1 = C_2H_5$) |
| 37 | $R^1 = C_2H_5$ $R^2 = H$ $R^3 = $ 2-thenoyl | m/z: 668 (M$^+$) NMR: 3.58 (1 H, d, J = 9.5 Hz) |
| 38 | $R^1 = C_2H_5$ $R^2 = H$ $R^3 = CO-(o-Cl-C_6H_4)$ | m/z: 696 (M$^+$) NMR: 3.59 (1 H, d, J = 9.5 Hz) |
| 39 | $R^1 = C_2H_5 + CH_3(2.5:1)$ $R^2 = H$ $R^3 = CO-(p-F-C_6H_4)$ | m/z: 680 (M$^+$, assigned to $R^1 = C_2H_5$) NMR: 3.58 (1 H, d, J = 9.5 Hz, assigned to $R^1 = CH_3$), 3.59 (1 H, d, J = 9.5 Hz, assigned to $R^1 = C_2H_5$) |
| 40 | $R^1 = C_2H_5$ $R^2 = H$ $R^3 = CO-(o-F-C_6H_4)$ | m/z: 680 (M$^+$) NMR: 3.59 (1 H, d, J = 9.5 Hz) |
| 41 | $R^1 = C_2H_5$ $R^2 = H$ $R^3 = $ isonicotinoyl | m/z: 663 (M$^+$) NMR: 3.59 (1 H, d, J = 9.2 Hz) |
| 42 | $R^1 = C_2H_5 + CH_3(2.2:1)$ $R^2 = H$ $R^3 = CO-(m-F-C_6H_4)$ | m/z: 680 (M$^+$, assigned to $R^1 = C_2H_5$) NMR: 3.58 (1 H, d, J = 9.5 Hz, assigned to $R^1 = CH_3$), 3.59 (1 H, d, J = 9.5 Hz, assigned to $R^1 = C_2H_5$) |
| 43 | $R^1 = C_2H_5$ $R^2 = H$ $R^3 = CO-(p-NO_2-C_6H_4)$ | m/z: 707 (M$^+$) NMR: 3.60 (1 H, d, J = 9.5 Hz) |

EXAMPLE 44

8,9-Epoxy-5-O-thiocyanatoacetylmilbemycin $A_{4+3}$ [$R^1=C_2H_5+CH_3(2.6:1)$, $R^2=H$, $R^3=COCH_2SCN$]

A solution of 100 mg of 8,9-epoxy-5-O-bromacetyl-milbemycin $A_{4+3}$ (prepared as in Example 13) and 15 mg of potassium rhodanide in 0.5 ml of acetone was mixed with a catalytic amount of sodium iodide and allowed to react at room temperature for 3 hours. The mixture was poured into water and extracted with ethyl acetate. The extracts were washed with water and then with a saturated aqueous solution of sodium chloride and dried over anhydrous magnesium sulfate. The solvent was then removed by distillation under reduced pressure and the residue was subjected to column chromatography through silica gel, to give 7.21 mg of the title compound.

Mass spectrum (m/z): 657 (M$^+$, assigned to $R^1=C_2H_5$).

Nuclear Magnetic Resonance Spectrum (270 MHz, CDCl$_3$), C9H, δ ppm:

3.56 (1H, doublet, J=9.5 Hz, assigned to $R^1=CH_3$);
3.58 (1H, doublet, J=9.5 Hz, assigned to $R^1=C_2H_5$).

EXAMPLE 45

8,9-Epoxy-5-O-trifluoroacetylmilbemycin $A_4$
($R^1=C_2H_5$, $R^2=H$, $R^3=COCF_3$)

38 μl of trifluoroacetic anhydride were added to a solution of 100 mg of 8,9-epoxymilbemycin $A_4$ and 28.3 mg of pyridine in 20 ml of dry benzene, whilst ice-cooling, and the mixture was allowed to react at room temperature for 30 minutes. At the end of this time, the reaction mixture was poured into an aqueous solution of sodium bicarbonate and extracted with ethyl acetate. The extracts were washed with water and dried over anhydrous magnesium sulfate. The solvent was then removed by distillation under reduced pressure, and the residue was subjected to column chromatography through silica gel, to give 71.0 mg of the title compound.

Mass Spectrum (m/z): 654 ($M^+$)
Nuclear Magnetic Resonance Spectrum (270 MHz, $CDCl_3$), $C_9H$, δ ppm:
3.58 (1H, doublet, J=9.5 Hz).

EXAMPLE 46

8,9-Epoxy-5-O-(3-carboxypropionyl)milbemycin $A_4$
($R^1=C_2H_5$, $R^2=H$, $R^3=COCH_2CH_2COOH$)

100 mg of 8,9-epoxymilbemycin $A_4$, 54 mg of triethylamine and 27 mg of succinic anhydride were reacted in the same way as described in Example 45, to give 110 mg of the title compound.

Mass spectrum (m/z): 558 ($M^+ + 1$-$COCH_2CH_2COOH$).
Nuclear Magnetic Resonance Spectrum (270 MHz, $CDCl_3$), δ ppm:
2.6–2.8 (4H, multiplet, $COCH_2CH_2COOH$);
3.56 (1H, doublet, J=9.8 Hz, $C_9H$).

EXAMPLE 47

14,15-Epoxy-5-O-propionylmilbemycin $A_{4+3}$
[$R^1=C_2H_5+CH_3$ (3.3:1), $R^2=H$, $R^3=COC_2H_5$]

94 mg of m-chloroperbenzoic acid were added to a solution of 240 mg of 5-O-propionylmilbemycin $A_{4+3}$ (3:1) in 10 ml of dry methylene chloride, whilst ice-cooling, and the mixture was allowed to react at room temperature for 2 hours. At the end of this time, the reaction mixture was filtered and the filtrate was washed with an aqueous solution of sodium bicarbonate. The solvent was then removed by distillation under reduced pressure, and the residue was subjected to column chromatography through silica gel, to give 160 mg of the title compound.

Mass spectrum (m/z): 614 ($M^+$, assigned to $R^1=C_2H_5$).
Nuclear Magnetic Resonance Spectrum (270 MHz, $CDCl_3$) δ ppm:
2.59 (1H, doublet, J=9.2 Hz, $C_{15}H$);
5.75–5.95 (2H, multiplet, $C_9H$, $C_{10}H$).

Following a procedure similar to that described in Example 47, the compounds of Examples 48 and 49 were prepared

EXAMPLE 48

14,15-Epoxy-5-O-acetylmilbemycin $A_{4+3}$
[$R^1=C_2H_5+CH_3$ (2.5:1), $R^2=H$, $R^3=COCH_3$]

Mass spectrum (m/z): 600 ($M^+$, assigned to $R^1=C_2H_5$).

Nuclear Magnetic Resonance Spectrum (270 MHz, $CDCl_3$) δ ppm:
2.54 (1H, doublet, J=9.3 Hz, $C_{15}H$).

EXAMPLE 49

14,15-Epoxy-5-O-methylcarbamoylimilbemycin $A_4$
($R^1=C_2H_5$, $R^2=H$, $R^3=CONHCH_3$)

Mass spectrum (m/z): 615 ($M^+$).
Nuclear Magnetic Resonance Spectrum (270 MHz, $CDCl_3$) δ ppm:
2.61 (1H, doublet, J=9.3 Hz, $C_{15}H$).

EXAMPLE 50

8,9:14,15-Diepoxy-5-O-chloromethoxycarbonylmilbemycin $A_4$ ($R^1=C_2H_5$, $R^2=H$, $R^3=COOCH_2Cl$)

10 mg of m-chloroperbenzoic acid were added to a solution of 32 mg of 8,9-epoxy-5-O-chloromethoxycarbonylmilbemycin $A_4$ (prepared as in Example 18) in 1.1 ml of dry methylene chloride, whilst ice-cooling, and the mixture was allowed to react at room temperature for 5 hours. At the end of this time, the reaction mixture was filtered and the filtrate was washed with an aqueous solution of sodium bicarbonate. The solvent was then removed by distillation under reduced pressure and the residue was subjected to column chromatography through silica gel, to give 13 mg of the title compound.

Mass spectrum (m/z): 666 ($M^+$, assigned to Cl=35).
Nuclear Magnetic Resonance Spectrum (270 MHz, $CDCl_3$) δ ppm:
2.66 (1H, doublet, J=9.9 Hz, $C_{15}H$):
3.53 (1H, doublet, J=9.5 Hz, $C_9H$).

Following a procedure similar to that described in Example 50, the following compounds of formula (Ib):

in which $R^1$, $R^2$ and $R^3$ are as defined in the following Table, were prepared. The nuclear magnetic resonance spectrum are reported only for the hydrogen atoms at $C_9$ and $C_{15}$.

| Examples | $R^1$ $R^2$ $R^3$ | m/z NMR ($C_9H$ and $C_{15}H$) |
|---|---|---|
| 51 | $R^1 = C_2H_5$ $R^2 = H$ $R^3 = COCH_2Cl$ | m/z: 650 ($M^+$, assigned to Cl = 35) $C_9H$: 3.42 (1 H, d, J = 9.35 Hz), $C_{15}H$: 2.55 (1 H, d, J = 9.5 Hz) |
| 52 | $R^1 = C_2H_5 + CH_3(4:1)$ $R^2 = H$ | m/z: 664 ($M^+$, assigned to $R^1 = C_2H_5$ & Cl = 35) $C_9H$: 3.53 (1 H, d, |

-continued

| Examples | R¹ R² R³ | m/z NMR (C₉H and C₁₅H) |
|---|---|---|
| | R³ = COCHClCH₃ | J = 9.5 Hz)<br>C₁₅H: 2.66 (1 H, d, J = 9.2 Hz) |
| 53 | R¹ = C₂H₅ + CH₃(1.7:1)<br>R² = H<br>R³ = COC₆H₅ | m/z: 556 (M⁺ +1 − COC₆H₅—H₂O, assigned to R¹ = C₂H₅)<br>C₉H: 3.54 (1 H, d, J = 9.5 Hz, assigned to R¹ = CH₃), 3.56 (1 H, d, J = 9.5 Hz, assigned to R¹ = C₂H₅)<br>C₁₅H: 2.66 (1 H, d, J = 9 Hz) |
| 54 | R¹ = C₂H₅ + CH₃(2.6:1)<br>R² = H<br>R³ = COCH₃ | m/z: 616 (M⁺, assigned to R¹ = C₂H₅)<br>C₉H: 3.54 (1 H, d, J = 9 Hz)<br>C₁₅H: 2.63 (1 H, d, J = 9.5 Hz) |
| 55 | C₂H₅ + CH₃ (2.6:1)<br>R² = H<br>R³ = COC₂H₅ | m/z: 630 (M⁺, assigned to R¹ = C₂H₅)<br>C₉H: 3.52 (1 H, d, J = 9.5 Hz)<br>C₁₅H: 2.66 (1 H, d, J = 9.9 Hz) |

EXAMPLE 56

Acaricidal activity against Tetranychus urticae

The primary leaves of cowpea plants of the species Vigna sinensis Savi were infected with organic phosphate-sensitive mites (*Tetranychus urticae*). One day after infection, the infested plants were sprayed, using a Mizuho rotary sprayer, with 7 ml of a test solution containing the compound under test at a concentration of 3 ppm, at a rate of 3.5 mg of the test solution per 1 cm² of leaf. The plants were assessed after 3 days by examining adult mites, under a binocular microscope, to determine living and dead individuals. Two plants were used for each concentration and each test compound. The plants were kept during the test in greenhouse compartments at 25° C. The results are reported in the following Table.

| Compound of Example No. | Lethal (%) |
|---|---|
| 1 | 98 |
| 2 | 100 |
| 12 | 56 |
| 15 | 100 |
| 17 | 94 |
| 18 | 97 |
| 21 | 94 |
| 22 | 60 |
| 24 | 69 |
| 32 | 73 |
| 35 | 86 |
| 37 | 77 |
| 45 | 100 |
| 48 | 67 |
| 52 | 71 |
| 54 | 71 |
| 55 | 99 |
| Control Compound 1 | 40 |
| Control Compound 2 | 45 |
| Control Compound 3 | 33 |
| Control Compound 4 | 31 |
| Control Compound 5 | 17 |
| Control Compound 6 | 63 |
| Control Compound 7 | 21 |

The Control compounds were as follows:

1. Milbemycin A₄
2. 8,9-Epoxymilbemycin A₄
3. 14,15-Epoxymilbemycin A₄
4. 8,9:14,15-Diepoxymilbemycin A₄
5. 5-O-acetylmilbemycin A₄
6. 5-O-propionylmilbemycin A₄₊₃ (3:1)
7. 5-O-chloroacetylmilbemycin A₄₊₃ (3:1)

As can be seen clearly from the above results, the compounds of the present invention have a far stronger acaricidal activity than that of natural milbemycin A₄ as well as stronger activities than the corresponding unesterified epoxymilbemycins or unepoxidized acylmilbemycins.

In more detail, the acaricidal effect of Control Compound 2 (in which milbemycin A₄, Control Compound 1, was epoxidized at the 8,9 position) was intensified slightly from 40% for Control Compound 1 to 45% for Control Compound 2, whilst the acaricidal effect of Control Compound 5 (the acetylated derivative of Control Compound 1) was actually reduced from the value of 40% achieved for Control Compound 1 to 17% for Control Compound 5. On the contrary, the acaricidal effect of the compound of Example 1 of the present invention was remarkably improved from the 40% of Control Compound 1 to 98%.

EXAMPLE 57

Nematocidal Activity Against *Nippostrongylus Brasiliensis*

0.1 ml of an aqueous solution containing the compound under test at a variety of concentration was added to 0.4 ml of a suspension of trichogenous nematodes (*Nippostrongylus brasiliensis*) which are parasitic on wild rats and had been previously cultured and hatched. 24 hours after this addition, the motility of the nematodes was checked by microscopic examination and the minimum inhibitory concentrations (MIC) of each of the test compounds was calculated. The MIC values for the compounds of Examples 1 and 15 were both 1.25 μg/ml, whilst those of the compounds of Examples 2, 45 and 47 were all 0.63 μg/ml.

We claim:

1. A compound of formula (I):

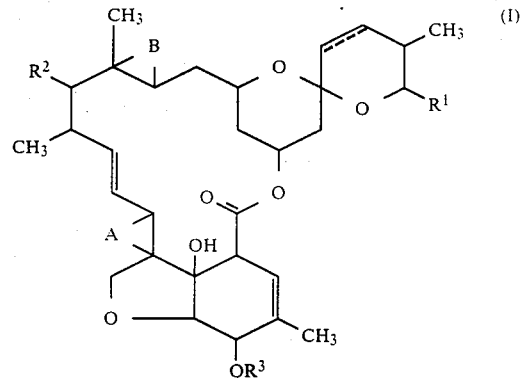

in which:
the broken line represents a single or double carbon-carbon bond between the carbon atoms at the 22 and 23 positions:
R¹ represents an isopropyl group or a sec-butyl group;

R² represents a 4'-(α-L-oleandrosyl)-α-L-oleandrosyloxy group;

A represents an oxygen atom;

B represents a double bond between the two carbon atoms to which it is shown as attached; and R³ represents a group of formula:

—CO—(O)ₙ—R⁴ in which:

n represents the cypher 0 or the integer 1; and

R⁴ represents a $C_1$–$C_{18}$ alkyl group, a $C_3$–$C_8$ cycloalkyl group, a $C_7$–$C_9$ aralkyl group, a $C_2$–$C_{17}$ alkenyl group, a $C_2$–$C_6$ alkynyl group, a $C_6$–$C_{10}$ aryl group of a heterocyclic group having from 5 to 10 ring atoms of which at least one is a hetero-atom selected from the group consisting of nitrogen, oxygen and sulfur atoms, said alkyl, alkenyl and alkynyl groups being unsubstituted or having at least one substituent selected from the group consisting of substituents (a):

substituents (a): alkoxy groups, halogen atoms, alkoxycarbonyl groups, carboxylic acyloxy groups, hydroxy groups, carboxy groups, amino groups, alkylamino groups, dialkylamino groups, trialkylamino groups, carboxylic acylamino groups, cyano groups, carbamoyl groups, alkylcarbamoyl groups, dialkylcarbamoyl groups, mercapto groups, alkylthio groups, alkylsulfinyl groups, alkylsulfonyl groups, nitro groups, phenoxy groups, halophenoxy groups, alkylsulfonyloxy groups, arylsulfonyloxy groups, thiocyanato groups and heterocyclic groups having 5 or 6 ring atoms of which at least one is a hetero-atom selected from the group consisting of nitrogen, oxygen and sulfur atoms;

and said cycloalkyl, aralkyl and aryl groups being unsubstituted or having at least one substituent selected from the group consisting of substituents (a) and substituents (b):

substituents (b): alkyl groups, alkoxyalkyl groups and haloalkyl groups;

and said heterocyclic groups being unsubstituted or having at least one substituent selected from the group consisting of substituents (a), substituents (b) and oxygen atoms;

where groups in said substituents (a) and substituents (b) contain carbon atoms, the maximum number of carbon atoms in each such group is 9 and said groups defined in substituents (a) and substituents (b) being unsubstituted or having at least one further substituent selected from the group consisting of substituents (a) and substituents (b) provided said further substituent is not itself further substituted; or R³ represents a group of formula:

—CO—NR⁵R⁶ in which R⁵ and R⁶ are independently selected from the group consisting of hydrogen atoms, $C_1$–$C_6$ alkyl groups, $C_2$–$C_6$ alkenyl groups, $C_7$–$C_9$ aralkyl groups and $C_6$–$C_{10}$ aryl groups, said groups being unsubstituted or having at least one substituent selected, in the case of said alkyl and alkenyl groups, from the group consisting of substituents (a) and, in the case of said aralkyl and aryl groups, from the group consisting of substituents (a) and substituents (b):

substituents (a): alkoxy groups, halogen atoms, alkoxycarbonyl groups, carboxylic acyloxy groups, hydroxy groups, carboxy groups, amino groups, alkylamino groups, dialkylamino groups, trialkylamino groups, carboxylic acylamino groups, cyano groups, carbamoyl groups, alkylcarbamoyl groups, dialkylcarbamoyl groups, mercapto groups, alkylthio groups, alkylsulfinyl groups, alkylsulfonyl groups, nitro groups, phenoxy groups, halophenoxy groups, alkylsulfonyloxy groups, arylsulfonyloxy groups, thiocyanato groups and heterocyclic groups having 5 or 6 ring atoms of which at least one is a hetero-atom selected from the group consisting of nitrogen, oxygen and sulfur atoms;

substituents (b): alkyl groups, alkoxyalkyl groups and haloalkyl groups;

where groups in said substituents (a) and substituents (b) contain carbon atoms, the maximum number of carbon atoms in each such group is 9 and said groups defined in substituents (a) and substituents (b) being unsubstituted or having at least one further substituent selected from the group consisting of substituents (a) and substituents (b) provided said further substituent is not itself further substituted; or R³ represents a group of formula:

—SO₂R⁷ in which R⁷ represents a $C_1$–$C_6$ alkyl group or a $C_6$–$C_{10}$ aryl group, said groups being unsubstituted or having at least one substituent selected, in the case of said alkyl group, from the group consisting of substituents (a) and, in the case of said aryl group, from the group consisting of substituents (b):

substituents (a): alkoxy groups, halogen atoms, alkoxycarbonyl groups, carboxylic acyloxy groups, hydroxy groups, carboxy groups, amino groups, alkylamino groups, dialkylamino groups, trialkylamino groups, carboxylic acylamino groups, cyano groups, carbamoyl groups, alkylcarbamoyl groups, dialkylcarbamoyl groups, mercapto groups, alkylthio groups, alkylsulfinyl groups, alkylsulfonyl groups, nitro groups, phenoxy groups, halophenoxy groups, alkylsulfonyloxy groups, arylsulfonyloxy groups, thiocyanato groups and heterocyclic groups having 5 or 6 ring atoms of which at least one is a hetero-atom selected from the group consisting of nitrogen, oxygen and sulfur atoms;

substituents (b): alkyl groups, alkoxyalkyl groups and haloalkyl groups;

where groups in said substituents (a) and substituents (b) contain carbon atoms, the maximum number of carbon atoms in each such group is 9 and said group defined in substituents (a) and substituents (b) being unsubstituted or having at least one further substituent selected from the group consisting of substituents (a) and substituents (b) provided said further substituent is not itself further substituted; or R³ represents a group of formula:

—(Y¹=)P(—Y²—R⁸)—Y³—R⁹ in which:

Y¹, Y² and Y³ are independently selected from the group consisting of oxygen atoms and sulfur atoms; and R⁸ and R⁹ are independently selected from the group consisting of $C_1$–$C_6$ alkyl groups and $C_1$–$C_6$ alkyl groups having at least one substituent selected from the group consisting of substituents (a):

substituents (a): alkoxy groups, halogen atoms, alkoxycarbonyl groups, carboxylic acyloxy groups, hydroxy groups, carboxy groups, amino groups, alkylamino groups, dialkylamino groups, trialkylamino groups, carboxylic acylamino groups, cyano groups, carbamoyl groups, alkylcarbamoyl groups, dialkylcarbamoyl groups, mercapto groups, alkylthio groups, alkylsulfinyl groups, alkylsulfonyl groups, nitro groups, phenoxy groups, halophenoxy groups, alkylsulfonyloxy groups, arylsulfonyloxy groups, thiocyanato groups and heterocyclic groups having 5 or 6 ring atoms of which at least one is a hetero-atom selected from the group consisting of nitrogen, oxygen and sulfur atoms;

where groups in said substituents (a) contain carbon atoms, the maximum number of carbon atoms in each such group is 9 and said groups defined in substituents (a) being unsubstituted or having at least one further substituent selected from the group consisting of substituents (a) and substituents (b) provided said further substituent is not itself further substituted;

substituents (b): alkyl groups, alkoxyalkyl groups and haloalkyl groups; or

R³ is selected from the group consisting of acetyl, propionyl, chloroacetyl, trichloroacetyl, trifluoroacetyl, acetoxyacetyl, chloropropionyl, chlorobenzoyl, ethoxycarbonyl, methoxycarbonyl, chloromethoxycarbonyl, dichloromethoxycarbonyl, (3,4-dihydro-2H-pyran-2-carbonyloxy)methoxycarbonyl, (3,4,5,6-diisopropylidene-D-galacturonyloxy)methoxycarbonyl, (2,2-dimethyl-1,3-dioxolanylmethoxy)methoxycarbonyl, hydroxybutyryloxymethoxycarbonyl, carboxypropionyl, (1H-1,2,4-triazol-1-yl)acetyl, diethylaminoacetyl, (iodomethyldiethylammonio)acetyl, methylcarbamoyl, ethylcarbamoyl, dimethylcarbamoyl, diethylcarbamoyl, methanesulfonyl, p-toluenesulfonyl, benzenesulfonyl, diethylthiophosphoryl, dimethylphosphoryl, diethylphosphoryl, fluorobenzoyl, butyryl, valeryl, hexanoyl, octanoyl, hexadecanoyl, isobutyryl, isovaleryl, pivaloyl, acryloyl, benzoyl, bromoacetyl, allyloxycarbonyl, iodoacetyl, propionyloxyacetyl, hydroxyacetoxyacetyl, (benzamidoacetoxy)acetyl, cinnamoyl, (trifluoromethyl)benzoyl, iodobenzoyl, toluoyl, methoxybenzoyl, dichlorobenzoyl, (chlorobenzyloxy)acetyl, (pyrrolylcarbonyloxy)acetyl, fluorobenzoyl, nicotinoyl, isonicotinoyl, picolinoyl, nitrobenzoyl and thiocyanatoacetyl groups.

2. A compound of formula (I):

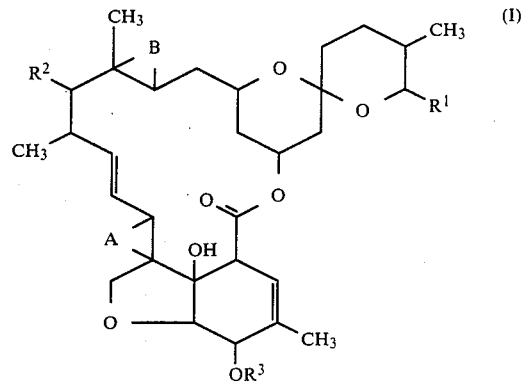

in which:

the broken line represents a single or double carbon-carbon bond between the carbon atoms at the 22 and 23 positions;

R¹ represents a methyl group, an ethyl group, an isopropyl group or a sec-butyl group;

R² represents a hydrogen atom or a 4'-(α-L-oleandrosyl)-α-L-oleandrosyloxy group;

A represents an oxygen atom;

B represents a double bond between the two carbon atoms to which it is shown as attached; and R³ represents a group of formula:

$$-CO-NR^5R^6$$

in which R⁵ and R⁶ are independently selected from the group consisting of hydrogen atoms, $C_1$–$C_6$ alkyl groups, $C_2$–$C_6$ alkenyl groups, $C_7$–$C_9$ aralkyl groups and $C_6$–$C_{10}$ aryl groups, said groups being unsubstituted or having at least one substituent selected, in the case of said alkyl and alkenyl groups, from the group consisting of substituents (a) and, in the case of said aralkyl and aryl groups, from the group consisting of substituents (a) and substituents (b):

substituents (a): alkoxy groups, halogen atoms, alkoxycarbonyl groups, carboxylic acyloxy groups, hydroxy groups, carboxy groups, amino groups, alkylamino groups, dialkylamino groups, trialkylamino groups, carboxylic acylamino groups, cyano groups, carbamoyl groups, alkylcarbamoyl groups, dialkylcarbamoyl groups, mercapto groups, alkylthio groups, alkylsulfinyl groups, alkylsulfonyl groups, nitro groups, phenoxy groups, halophenoxy groups, alkylsulfonyloxy groups, arylsulfonyloxy groups, thiocyanato groups and heterocyclic groups having 5 or 6 ring atoms of which at least one is a hetero-atom selected from the group consisting of nitrogen, oxygen and sulfur atoms;

substituents (b): alkyl groups, alkoxyalkyl groups and haloalkyl groups;

where groups in said substituents (a) and substituents (b) contain carbon atoms, the maximum number of carbon atoms in each such group is 9 and said groups defined in substituents (a) and substituents (b) being unsubstituted or having at least one further substituent selected from the group consisting of substituents (a) and substituents (b) provided said further substituent is not itself further substituted.

3. A compound of formula (I):

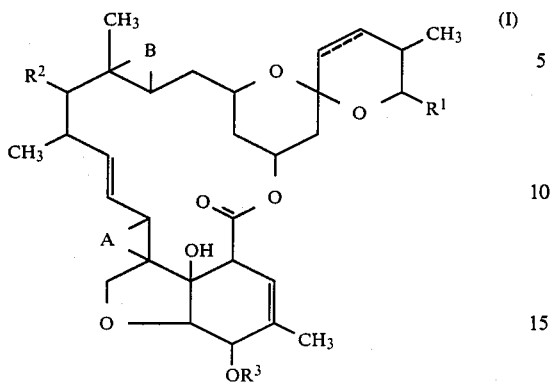

in which:
the broken line represents a single or double carbon-carbon bond between the carbon atoms at the 22 and 23 positions;
$R^1$ represents a methyl group, an ethyl group, an isopropyl group or a sec-butyl group;
$R^2$ represents a hydrogen atom or a 4'-(α-L-oleandrosyl)-α-L-oleandrosyloxy group;
A represents an oxygen atom;
B represents double bond between the two carbon atoms to which it is shown as attached; and
$R^3$ represents a group of formula:

$-SO_2R^7$ in which $R^7$ represents a $C_1$-$C_6$ alkyl group or a $C_6$-$C_{10}$ aryl group, said groups being unsubstituted or having at least one substituent selected, in the case of said alkyl group, from the group consisting of substituents (a) and, in the case of said aryl group, from the group consisting of substituents (b):
substituents (a): alkoxy groups, halogen atoms, alkoxycarbonyl groups, carboxylic acyloxy groups, hydroxy groups, carboxy groups, amino groups, alkylamino groups, dialkylamino groups, trialkylamino groups, carboxylic acylamino groups, cyano groups, carbamoyl groups, alkylcarbamoyl groups, dialkylcarbamoyl groups, mercapto groups, alkylthio groups, alkylsulfinyl groups, alkylsulfonyl groups, nitro groups, phenoxy groups, halophenoxy groups, alkylsulfonyloxy groups, arylsulfonyloxy groups, thiocyanato groups and heterocyclic groups having 5 or 6 ring atoms of which at least one is a hetero-atom selected from the group consisting of nitrogen, oxygen and sulfur atoms;
substituents (b): alkyl groups, alkoxyalkyl groups and haloalkyl groups; where groups in said substituents (a) and substituents (b) contain carbon atoms, the maximum number of carbon atoms in each such group is 9 and said groups defined in substituents (a) and substituents (b) being unsubstituted or having at least one further substituent selected from the group consisting of substituents (a) and substituents (b) provided said further substituent is not itself further substituted.

4. A compound of formula (I):

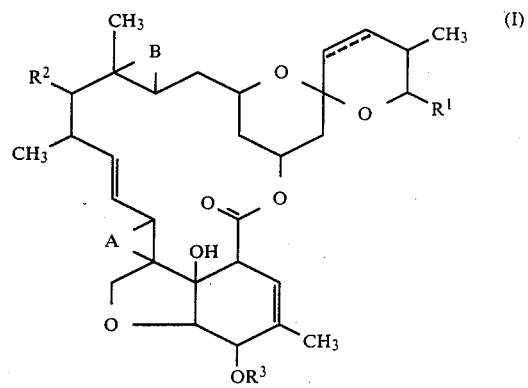

in which:
the broken line represents a single or double carbon-carbon bond between the carbon atoms at the 22 and 23 positions;
$R^1$ represents a methyl group, an ethyl group, an isopropyl group of a sec-butyl group;
$R^2$ represents a hydrogen atom or a 4'-(α-L-oleandrosyl)-α-L-oleandrosyloxy group;
A represents an oxygen atom;
B represents a double bond between the two carbon atoms to which it is shown as attached; and
$R^3$ represents a group of formula:

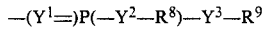
$-(Y^1=)P(-Y^2-R^8)-Y^3-R^9$ in which:
$Y^1$, $Y^2$ and $Y^3$ are independently selected from the group consisting of oxygen atoms and sulfur atoms; and
$R^8$ and $R^9$ are independently selected from the group consisting of $C_1$-$C_6$ alkyl groups and $C_1$-$C_6$ alkyl groups having at least one substituent selected from the group consisting of substituents (a):
substituents (a): alkoxy groups, halogen atoms, alkoxycarbonyl groups, carboxylic acyloxy groups, hydroxy groups, carboxy groups, amino groups, alkylamino groups, dialkylamino groups, trialkylamino groups, carboxylic acylamino groups, cyano groups, carbamoyl groups, alkylcarbamoyl groups, dialkylcarbamoyl groups, mercapto groups, alkylthio groups, alkylsulfinyl groups, alkylsulfonyl groups, nitro groups, phenoxy groups, halophenoxy groups, alkylsulfonyloxy groups, arylsulfonyloxy groups, thiocyanato groups and heterocyclic groups having 5 or 6 ring atoms of which at least one is a hetero-atom selected from the group consisting of nitrogen, oxygen and sulfur atoms;
where groups in said substituents (a) contain carbon atoms, the maximum number of carbon atoms in each such group is 9 and said groups defined in substituents (a) being unsubstituted or having at least one further substituent selected from the group consisting of substituents (a) and substituents (b) provided said further substituent is not itself further substituted;
substituents (b): alkyl groups, alkoxyalkyl groups and haloalkyl groups.

5. A compound as claimed in claim 1, wherein the broken line between the 22 and 23 positions represents a single bond, $R^1$ represents an isopropyl group or a sec-butyl group and R² represents a 4′-(α-L-oleandrosyl)-α-L-oleandrosyloxy group.

6. A compound as claimed in claim 1, wherein the broken line between the 22 and 23 positions represents a double bond, R¹ represents an isopropyl group or a sec-butyl group and R² represents a 4′-(α-L-oleandrosyl)-α-L-oleandrosyloxy group.

7. A compound as claimed in claim 1, wherein R³ represents a group of formula:

$$-(Y^1=)P(-Y^2-R^8)-Y^3-R^9$$

in which:
  Y¹, Y² and Y³ are independently selected from the group consisting of oxygen atoms and sulfur atoms; and
  R⁸ and R⁹ are independently selected from the group consisting of $C_1$–$C_6$ alkyl groups and $C_1$–$C_6$ alkyl groups having at least one substituent selected from the group consisting of substituents (a):
  substituents (a): alkoxy groups, halogen atoms, alkoxycarbonyl groups, carboxylic acyloxy groups, hydroxy groups, carboxy groups, amino groups, alkylamino groups, dialkylamino groups, trialkylamino groups, carboxylic acylamino groups, cyano groups, carbamoyl groups, alkylcarbamoyl groups, dialkylcarbamoyl groups, mercapto groups, alkylthio groups, alkylsulfinyl groups, alkylsulfonyl groups, nitro groups, phenoxy groups, halophenoxy groups, alkylsulfonyloxy groups, arylsulfonyloxy groups, thiocyanato groups and heterocyclic groups having 5 or 6 ring atoms of which at least one is a hetero-atom selected from the group consisting of nitrogen, oxygen and sulfur atoms;
  where groups in said substituents (a) contain carbon atoms, the maximum number of carbon atoms in each such group is 9 and said groups defined in substituents (a) being unsubstituted or having at least one further substituent selected from the group consisting of substituents (a) and substituents (b) provided said further substituent is not itself further substituted;
  substituents (b): alkyl groups, alkoxyalkyl groups and haloalkyl groups.

8. A compound designated 8,9-epoxy-5-O-propionylmilbemycin $A_{4+3}$.

9. A compound designated 8,9-epoxy-5-O-α-chloropropionylmilbemycin $A_{4+3}$.

10. A compound designated 8,9-epoxy-5-O-trifluoroacetylmilbemycin $A_4$.

11. An anti-parasitic composition comprising an anti-parasitic effective amount of the compound of claim 2 in an acceptable carrier.

12. An anti-parasitic composition comprising an anti-parasitic effective amount of the compound of claim 3 in an acceptable carrier.

13. An anti-parasitic composition comprising an anti-parasitic effective amount of the compound of claim 4 in an acceptable carrier.

14. A method of treating a plant against damage by parasites selected from the group consisting of acarids, helminths and insects which comprise applying an effective amount of the compound of claim 2 to said plant or the seeds of said plant.

15. A method of treating a plant against damage by parasites selected from the group consisting of acarids, helminths and insects which comprise applying an effective amount of the compound of claim 3 to said plant or the seeds of said plant.

16. A method of treating a plant against damage by parasites selected from the group consisting of acarids, helminths and insects which comprise applying an effective amount of the compound of claim 4 to said plant or the seeds of said plant.

17. A method of treating an animal against damage by parasites selected from the group consisting of acarids, helminths and insects which comprise applying an effective amount of the compound of claim 2 to said animal.

18. A method of treating an animal against damage by parasites selected from the group consisting of acarids, helminths and insects which comprise applying an effective amount of the compound of claim 3 to said animal.

19. A method of treating an animal against damage by parasites selected from the group consisting of acarids, helminths and insects which comprise applying an effective amount of the compound of claim 4 to said animal.

* * * * *